(12) United States Patent
Raja et al.

(10) Patent No.: US 7,998,568 B2
(45) Date of Patent: Aug. 16, 2011

(54) BIOCERAMIC COATED APPARATUS AND METHOD OF FORMING THE SAME

(75) Inventors: Krishnan Selva Raja, Sparks, NV (US); Manoranjan Misra, Reno, NV (US); Archana Kar, Reno, NV (US)

(73) Assignee: Board of Regents of the Nevada System of Higher Education, on Behalf of the University of Nevada, Reno, Reno, NV (US)

( * ) Notice: Subject to any disclaimer, the term of this patent is extended or adjusted under 35 U.S.C. 154(b) by 555 days.

(21) Appl. No.: 11/570,935

(22) PCT Filed: Jun. 27, 2005

(86) PCT No.: PCT/US2005/022796
§ 371 (c)(1),
(2), (4) Date: Dec. 5, 2008

(87) PCT Pub. No.: WO2006/004686
PCT Pub. Date: Jan. 12, 2006

(65) Prior Publication Data
US 2009/0082865 A1    Mar. 26, 2009

Related U.S. Application Data

(60) Provisional application No. 60/582,548, filed on Jun. 25, 2004.

(51) Int. Cl.
B32B 3/26      (2006.01)
A61F 2/02      (2006.01)
C25D 11/34     (2006.01)
(52) U.S. Cl. ............... 428/305.5; 428/306.6; 428/307.7; 428/312.2; 428/315.5; 428/469; 428/702; 428/704; 623/11.11; 623/16.11; 205/150; 205/171; 427/2.1
(58) Field of Classification Search ........................ None
See application file for complete search history.

(56) References Cited

U.S. PATENT DOCUMENTS

| | | |
|---|---|---|
| 2002/0122828 A1 | 9/2002 | Liu |
| 2003/0152606 A1 | 8/2003 | Gerber |
| 2004/0031519 A1 | 2/2004 | Andriessen |

*Primary Examiner* — Ling Xu
(74) *Attorney, Agent, or Firm* — J.A. Lindeman & Co., PLLC

(57) ABSTRACT

The invention relates to a bioceramic coated apparatus and method of forming the same. The apparatus may be a medical implant such as, for example, an orthopedic implant or a dental implant. The bioceramic coating is designed to increase tissue and/or bone growth upon implantation of the apparatus. The apparatus has a valve metal substrate having a nanoporous valve metal oxide surface layer. The nanoporous surface layer contains a plurality of nanopores. The nanopores have adsorbed phosphate ions on at least their interior surfaces. A bioceramic coating is formed on the nanoporous surface and anchored into the nanopores. Optionally, the nanopores are formed into a tapered shape in order to increase adhesion to the bioceramic coating.

30 Claims, 13 Drawing Sheets

BIOCERAMIC COATED APPARATUS AND METHOD OF FORMING THE SAME

CROSS REFERENCE TO RELATED DOCUMENTS

This application claims priority under 35 U.S.C. §119 to U.S. Provisional Patent Application Ser. No. 60/582,548, filed Jun. 25, 2004; the entire disclosure of which is incorporated by reference.

BACKGROUND OF THE INVENTION

1. Field of the Invention

This invention relates to a bioceramic coated apparatus and a method for forming the same on a nanoporous valve metal substrate. More particularly, the invention is directed to a method of forming a nanoporous valve metal substrate having a bioceramic coating formed thereon for use as a medical implant.

2. Background of the Invention

Calcium phosphate coatings have received much attention as the coatings have excellent biocompatibility properties and are widely used on medical implants including dental and orthopedic implants. For example, the coatings have excellent osseointegration properties. Several coating methods such as plasma spray, sol-gel, electrophoretic, RF sputtering and electrochemical deposition are being used to coat implant surfaces as described in M. C. Kuo, S. K. Yen, *The Process of Electrochemical Deposited Hydroxyapatite Coatings On Biomedical Titanium at Room Temperature*, Materials Science and Engineering, C, 20, (2002), pp. 153-160, which is incorporated by reference.

Plasma spray processes are currently widely used commercial methods for coating bioceramics on implants. However, coatings formed by plasma spray processes have several disadvantages, such as, micro-cracks, poor adhesion between the coating and substrate, phase changes due to high temperature exposure, non-uniformity in the coating density and improper microstructural control. These disadvantages may result in failure of the implanted system. See Rodriguez et al., *In Vitro Osteoblast Response to Anodized Titanium and Anodized Titanium Followed by Hydrothermal Treatment*, Biomed. Mater. Res., 37, (2003), pp. 352-358, which is incorporated by reference. Attempts have been made to improve the adhesion between the coating and the substrate. For example, in order to improve the adhesion between the bioceramic coatings and substrates, hydroxyapatite formation has been carried out in a series of hydrothermal treatments of anodized surface in a solution containing Ca and P. See Zhu, et al., *Characterization of Hydrothermally treated Anodic Oxides Containing Ca and P on Titanium*, J. Mat. Science: Materials in Medicine, 14, (2003), pp. 629-634, which is incorporated by reference. Anodic plasma chemical processes are another method to obtain and improve adhesion of anodized surfaces containing Ca and P. See Frauchiger, et al., *Anodic Plasma-Chemical Treatment of CP Titaniun Surfaces for Biomedical Applications*, Biomaterials, 25, (2004), pp. 593-606, which is incorporated by reference. However, in both the hydrothermally treated anodized surface process and the anodic plasma chemical process, there is discrete formation of apatite-like phases and the coating obtained is not uniform among other disadvantages. Also, in conventional anodic plasma chemical processes, the pores are formed during anodization at high voltages (e.g., >200 V) in calcium phosphate containing solutions. The pores were larger (1-5 microns diameter) and size of the pores was not uniform. Moreover, the large voltages leads during anodization resulted in dielectric breakdown of the oxide layer and internal microcracks. Subsequently, deposited hydroxyapatite crystals grown out of these discrete pores were not uniformly and densely distributed for better biocompatibility. Further, inherent defects of oxide film formed at higher anodization voltages over which hydroxyapatite crystals were formed lead to poor interfacial bond strength and poor bone integration.

A need therefore exists for improved bioceramic coated apparatuses and methods for making them. The apparatuses should have improved adhesion of the bioceramic coating.

SUMMARY OF THE INVENTION

The invention is directed to a method for forming nanopores on valve metal substrates and a bioceramic coating that substantially obviates one or more of the problems due to limitations and disadvantages of the prior art.

The invention relates to a bioceramic coated apparatus. The apparatus may be a medical implant such as, for example, an orthopedic implant or a dental implant. The bioceramic coating is designed to increase tissue and/or bone growth upon implantation of the apparatus. The apparatus has a valve metal substrate having a nanoporous valve metal oxide surface layer. The nanoporous surface layer contains a plurality of nanopores. The nanopores have adsorbed phosphate ions on at least their interior surfaces. A bioceramic coating is formed on the nanoporous surface and anchored into the nanopores. Optionally, the nanopores are formed into a tapered shape in order to increase adhesion to the bioceramic coating.

Another aspect of the invention is directed towards a method for forming a bioceramic coated apparatus. A valve metal substrate is anodized in a fluoride-containing phosphoric acid solution at a voltage and time sufficient to form a nanoporous valve metal oxide surface on the valve metal substrate. The nanopores have adsorbed phosphate ions on at least their interior surfaces. Next, the nanoporous valve metal oxide surface is contacted with a basic solution to raise the pH to or above about 6.7. The nanoporous valve metal oxide surface is immersed in an electrolyte solution containing calcium and phosphate ions. A calcium phosphate ceramic surface is electrodeposited on the nanoporous valve metal oxide surface.

Another aspect of the invention is directed towards a valve metal substrate having a nanoporous valve metal oxide layer and method of forming the that surface as a separate embodiment of the invention.

It is to be understood that both the foregoing general description and the following detailed description are exemplary and explanatory and are intended to provide further explanation of the invention as claimed.

BRIEF DESCRIPTION OF THE DRAWINGS

Aspects of the invention are illustrated in the figures of the accompanying drawings in which like reference numerals refer to similar elements and in which.

DETAILED DESCRIPTION OF THE PREFERRED EMBODIMENTS

Figure 1:
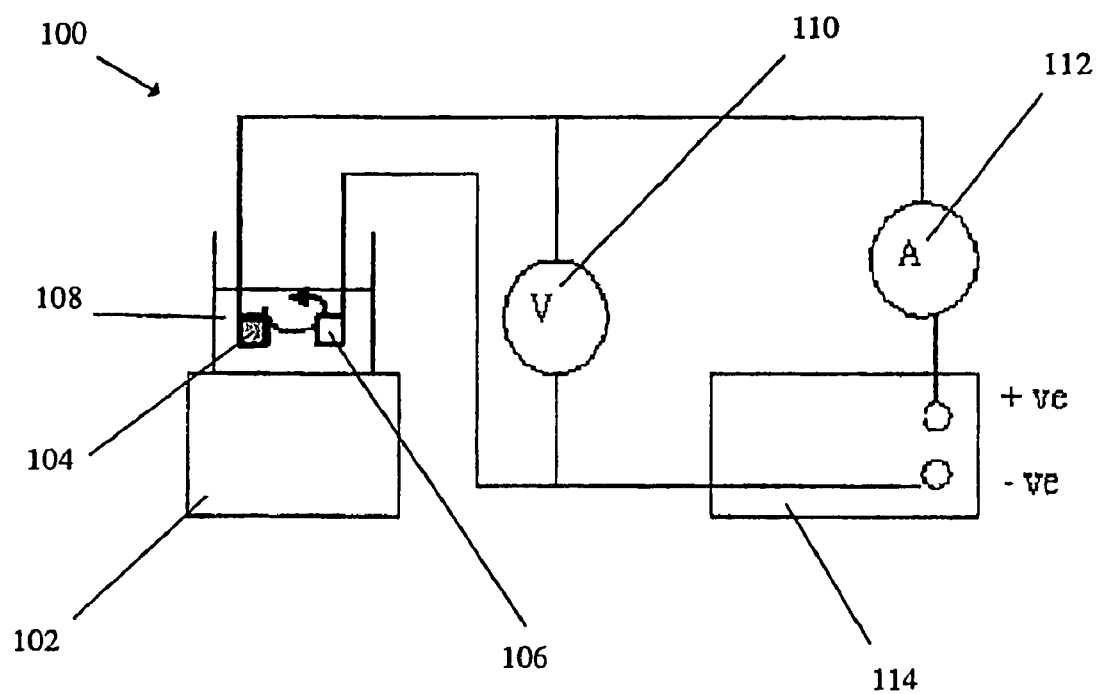
FIG. 1 shows a schematic of an anodization system according to an embodiment of the invention.

The invention relates to a bioceramic coated apparatus. The apparatus may be a medical implant such as, for example, an orthopedic implant or a dental implant. Any known bioceramic coating may be used in an apparatus of the invention. The bioceramic coating is provided for tissue and/or bone growth upon implantation of the apparatus, e.g., osseointegration. The apparatus has a valve metal substrate having a nanoporous valve metal oxide surface layer. The nanoporous surface layer contains a plurality of nanopores. The nanopores have adsorbed phosphate ions on at least their interior surfaces. The adsorbed phosphate ions on the walls of the nanopores aid in nucleation and thus, subsequent growth of bioceramic coating from the pores. A bioceramic coating is formed on the nanoporous surface and anchored into the nanopores. Optionally, the nanopores have a substantially tapered shape in order to increase adhesion to the bioceramic coating. In the tapered nanopores the bottom of the nanopore is wider than its top. The tapering may or may not be uniform throughout a particular nanopore or among a plurality of nanopores making up the nanoporous valve metal oxide surface.

Valve metal substrates which may be used in the invention include at least one of Ti, Ta, Nb, Hf, V, W, Zr, their alloys thereof, and/or combinations thereof. Preferably, the valve metal is Ti or Ti alloy due to its excellent biocompatible and mechanical properties. The valve metal substrate and/or its surface may be formed into any type of geometry known in the art. For example, the valve metal substrate may be curved, non-linear, bent, triangular, smooth, rough, indented, etc. Optionally, the valve metal substrate is formed on another substrate, such as, for example, a semiconductor substrate, plastic substrate, and the like, as known in the art. In a preferred embodiment, the valve metal substrate is the outer layer or the entirety of a medical implant.

As mentioned above, any bioceramic material known in the art to support tissue and/or bone growth may used as the bioceramic coating for an apparatus of the invention. For example, the coating may be any calcium phosphate coatings having a Ca/P ratio ranging from about 1.5 to 1.7, and more preferably, the Ca/P ratio is about 1.67. A Ca/P ratio of about 1.5 represents natural bone and a Ca/P ratio of about 1.67 corresponds to hydroxyapatite $[Ca_{10}(PO_4)(OH)_2]$, which is similar to the mineral component found in bones and teeth and is widely used in medical implants, such as dental and orthopedic implants. Hydroxyapatite is a preferred bioceramic coating for use with the invention.

The invention also relates to a method for forming a bioceramic coated apparatus. A valve metal substrate is anodized in a fluoride-containing phosphoric acid solution at a voltage and time sufficient to form a nanoporous valve metal oxide surface on the valve metal substrate. The nanopores have adsorbed phosphate ions on at least their interior surfaces. Next, the nanoporous valve metal oxide surface is contacted with a basic solution to raise the pH to or above about 6.7. The nanoporous valve metal oxide surface is immersed in an electrolyte solution containing calcium and phosphate ions. A calcium phosphate ceramic surface is electrodeposited on the nanoporous valve metal oxide surface.

The valve metal substrate may be cleaned and polished using standard metallographic cleaning and polishing techniques. For example, the valve metal substrate may be chemical mechanically polished as known in the art. Preferably, the valve metal surface may be incrementally polished by utilizing 120 grit emery paper down to 1200 grit emery paper followed by wet polishing in a 15 micron alumina slurry. After polishing, the valve metal substrate is thoroughly washed with distilled water and sonicated for about 10 minutes in isopropyl alcohol as known in the art. Performing such optional cleaning and polishing aids in consistency of the valve metal substrates used in the invention, that is, it ensures the valve metal substrates have uniform starting points (e.g., planar surfaces). It is noted that any native oxides on the valve metal substrates do not need to be removed in order for the valve metal substrate to be used in the invention.

To form the bioceramic coated apparatus of the invention, a valve metal substrate is anodized in a fluoride-containing phosphoric acid solution at a voltage and time sufficient to form a nanoporous valve metal oxide surface on the valve metal substrate. The nanopores have adsorbed phosphate ions on at least their interior surfaces.

The fluoride-containing phosphoric acid an aqueous solution having a phosphoric acid concentration ranging from about 0.1 M to about 5.0 M. This is the source of the phosphate ions which are adsorbed on surface of the nanopores. Higher concentrations of phosphoric acid are possible it was found that they may lead to non-uniform nanopores during the anodization process. Preferably, the phosphoric acid concentration ranges from about 0.2 M to 2.0 M and more preferably, the concentration ranges from about 0.5 M to 1.0 M. The fluoride ion concentration ranges from about 0.1 M to about 0.3 M and more preferably at about 0.14 M. The fluoride ion source is selected from compounds, such as, HF, NaF, KF, and $NH_4F$ and more preferably NaF salt. The selection of the fluoride source also may be selected by its degree of solubility in the phosphoric acid as known in the art. Preferably, the fluoride-containing phosphoric acid solution is an aqueous solution at 24-30° C. is 0.5 M $H_3PO_4$+0.14 M (NaF or HF) or at 19-20° C. is 0.5 M $H_3PO_4$+0.28 M (NaF or HF) using deionized water.

The fluoride-containing phosphoric acid solution is optimized with fluoride and phosphate ions, which aid in the formation of uniform nanopores and incorporation of phosphate ions on the wall of the pores, respectively. More specifically, the addition of fluoride or other suitable halide ions aids in the formation of nanopores having similar diameters determined by the applied voltage in the anodization process. If no fluoride ions are added the nanoporous structure is obtained by dielectric breakdown (e.g., application of high potentials in the range of 200-350 V) in which case the pore diameter and pore distribution will not be uniform and the oxide layer will have internal cracks and other defects due to the high potentials. Anodization in fluoride ions added to the phosphoric acid solution results in adsorbed phosphate ions in the nanoporous structure. Also, the adsorbed phosphate ions on the walls of the nanopores aids in the nucleation and thus, subsequent growth of bioceramic coating from the pores.

The anodization may be conducted in any conventional anodization system as known in the art. For example, an anodization system as represented in FIG. 1. Referring to FIG. 1, the system is generally depicted as element 100 and includes a magnetic stirrer 102, positive terminal 104, negative terminal 106, electrolyte solution 108, a voltage meter 110, ammeter 112, and a direct current (DC) power source 114. The DC power source 114 can supply up to 40 V or more of potential and support up to 20 mA/cm$^2$ or more current density. In a preferred embodiment, the valve metal substrate to be anodized is connected to the positive terminal 104 of the power source and a platinum foil (Pt rod/mesh) having an equal or larger area as compared to the valve metal substrate is connected to the negative terminal 106 of power source 114. An external volt meter 110 and an ammeter 112 are connected to the circuit in parallel and series respectively for measuring the actual potential and current during anodization. The distant between valve metal and Pt may be maintained at about 4 cm.

The anodization voltage and time is set to a predetermined value, which is sufficient to form a nanoporous valve metal oxide surface. The nanopores are formed having substantially uniform diameters in a nanotube like shape (e.g., cylindrical). The higher the anodization voltage the larger the diameter of the nanopores. Preferably, the anodization voltage ranges from about 5 to 40 V and the diameter ranges from about 10 to 300 nm. More specifically, applying 5 V corresponds to a diameter of about 10-20 nm, 10 V corresponds to a diameter of about 20 to 40 nm, 20 V corresponds to a diameter of about 60-100 nm, and 40 V corresponds to a diameter of about 150 to 200 nm. The longer the application of voltage the thicker the nanoporous valve metal oxide. The thickness is preferably in the range of 200 to 400 nm and more preferably in the range of about 250 to 300 nm. A thickness of about 400 nm appears to be the equilibrium thickness for this process. Preferably, the voltage is set at about 10 V for about 20 minutes to give a thickness of about 200 nm. During the anodization process the anodization electrolyte solution may be continuously stirred with the magnetic stirrer or other suitable device as known in the art.

Optionally, after the initial anodization, the voltage is increased at a rate sufficient to form the nanopores in a substantially tapered shape. In this step the voltage should be increased over the initial voltage used to for the nanopores. The tapering may or may not be uniform throughout a particular nanopore or among a plurality of nanopores making up the nanoporous valve metal oxide surface. Tapered nanopores are a particularly preferred embodiment of the invention. To form tapered nanopores the voltage, for example, may be increased in steps (e.g., linearly, steps, non-linear) at a rate to a higher voltage as compared to the initial anodization. Preferably, the voltage is increased at a constant rate of about 0.5 V/min to a higher voltage of about 20 to 25 V when the initial voltage was about 10 V. That is, preferably the voltage is increased to about 10 to 15 V higher than the initial voltage used in the anodization at a constant rate. This process results in increased diameter nanopores at or near the interface of the valve metal substrate and the valve metal oxide (e.g., 60-100 nm diameter), thereby forming nanopores having a substantially tapered shape. If tapered nanopores are not desired, uniform diameter nanotube like pores can be formed by applying a single potential, typically >20 V, as discussed above.

It is noted that long anodization times may not be detrimental to the resultant product as the anodization process reaches a steady state and hence the film thickness is constant after a certain length of time as determined from the current plateau. There is no maximum time limit in any of the steps of the anodization process. Also, as the anodization was carried out at lower voltages in fluoride-containing phosphoric acid solution, the mechanism of nanotube formation was not by dielectric breakdown of oxide. Therefore, the nanoporous valve metal oxide surface (e.g., titanium oxide layer) does not have internal microcracks, thereby ensuring good interfacial bonding between the valve metal substrate and its oxide.

After anodization, the nanoporous substrate is contacted with a basic solution to raise the pH to or above about 6.7. The pH is qualitatively determined as known in the art. The nanoporous substrate may first be washed in water (e.g., distilled or more preferably deionized water) prior contacting with the basic solution.

The basic solution may be any suitable base as known in the art. For example, the pH may be raised by immersing the anodized valve metal surface in a hydroxide solution, preferably at about 0.3 to 0.5 M NaOH, for about 15 minutes. This increases the pH from acidic to neutral or slightly basic inside the pores, which aids in the subsequent bioceramic coating formation. After the nanoporous substrate has been contacted with a basic solution it is washed in water.

Next, the nanoporous substrate is immersed in an aqueous electrolyte solution containing calcium and phosphate ions. The bioceramic coating is an electrodeposited calcium phosphate ceramic surface on the nanoporous valve metal oxide surface. Optionally, prior to deposition the nanoporous surface is cleaned in water and/or sonicated treatment in water as is known in the art. The bioceramic coatings of the invention are formed on the surfaces of nanopores and oxide surface and anchored into at least one of the plurality of nanopores. Thereby, adhesion is improved by forming the bioceramic coating in the nanopores as the tapered shape of the nanopore acts as a mechanical way to aid in the adhesion (e.g., anchor for the coating).

The aqueous electrolyte solution contains suitable calcium and phosphate ions, for example, calcium and phosphate salts to form a desired bioceramic coating. Typical salts may include $Ca(NO_3)_2$, calcium chloride, calcium acetate, $NH_4H_2PO_4$, calcium glycerophosphate, calcium phosphate tribasic powder, and combinations thereof. The solubility of the calcium and phosphate ions depends on the pH and temperature of the solution as known in the art. Also, the morphology of the deposited coating varies with pH. The pH of the solution is adjusted between about 4.0 to 6.0 by the addition of 1.0 M HCl acid to the solution. The morphology of the coating is affected by the solution pH. A solution having a near neutral pH results in hexagonal-rod like crystal growth, whereas, a solution having a lower pH results in flaky type growth. The electrolyte solution may also contain other salts, as electrolytes, or buffers as is known in the art.

In a preferred embodiment, the electrolyte solution includes 9.5 grams of Ca(NO$_3$)$_2$, 3.0 grams of NH$_4$H$_2$PO$_4$, 58.5 gram of NaCl, 5 grams of calcium phosphate tribasic powder in 1 L of deionized water at a pH of about 4.0 to 6.0. Alternately, the electrolyte solution contains calcium chloride, ammonium dihydrogen phosphate or sodium dihydrogen phosphate, sodium chloride, and about 0.05 M of Tris (trishydroxy-aminomethane) at a pH of about 7.0. The solution is prepared so that Ca/P ratio ranges from about 1.5 to 1.67. NaCl is used as a supporting electrolyte to increase the solution's conductivity as the Ca and P containing salt concentration is low (tens of milli-moles (mM)). Citric acid, ammonium hydroxide, hydrochloric acid are added to adjust the pH to 6-7.

Figure 2:
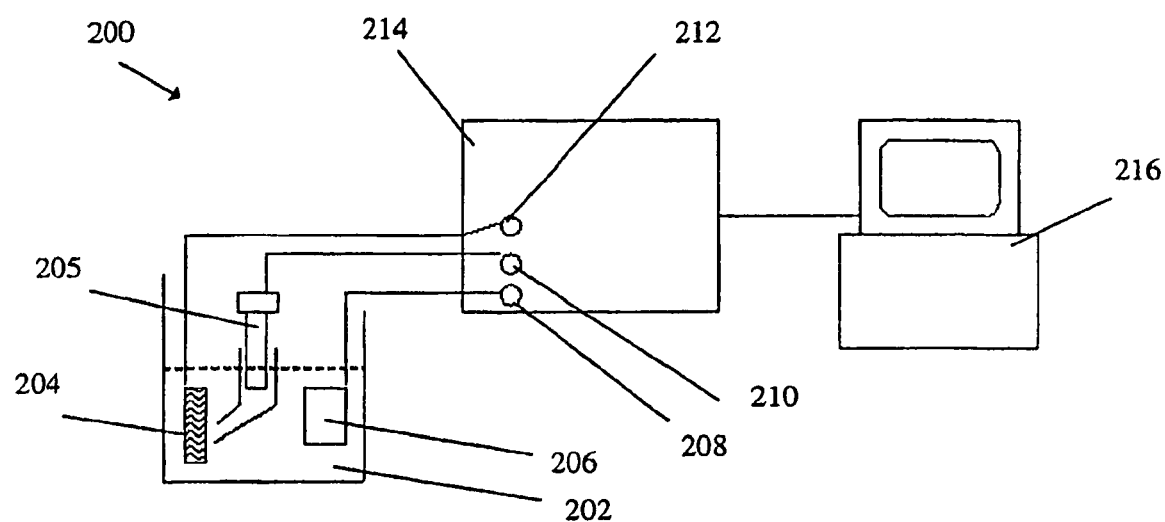
FIG. 2 shows a schematic of an electrochemical deposition system according to an embodiment of the invention.

The bioceramic coating may be electrodeposited to a thickness ranging from about 0.1 μm to 25 μm and more preferably about 2 to 10 μm. The electrodeposition may be conducted on any conventional apparatus as known in the art. In a preferred embodiment, a bioceramic coating is electrochemically deposited with an electrochemical deposition set-up as shown in FIG. 2. The electrochemical deposition set-up is generally depicted as reference number 200 and includes an electrolyte solution 202, a cathode 204, a counter electrode 206, and a reference electrode 205 (e.g., Ag/AgCl in saturated potassium chloride) these electrodes are in electrical communication with a potentiostat 214. The counter electrode 206 is a Pt foil or mesh with suitable surface area, normally larger than the working electrode surface. The potentiostat 214 is in electrical communication with a computer and computer controls the outputs to the cathode electrode 210, reference electrode output 212, and common electrode 208. The working electrode is in electrical coupled to the anodized Ti or Ti base material. The counter electrode is electrically coupled to the a Pt foil or mesh having suitable surface area. Preferably, the Pt foil or mesh has a larger surface area than the working electrode surface area.

The electrodeposition may include applying a constant current and/or potential during the deposition. Also, the electrodeposition may include applying a pulsed current and/or potential during the deposition, which allows for improved deposition at the bottom of the tapered nanopores (e.g., nucleation of calcium phosphate crystals at the bottom of the oxide nanotubes). Pulsing the current is preferred to pulsing the potential as sometimes potential pulses result in cracking of nanoporous oxide layer. The mode of operation (e.g., current control or potential control) depends on the capability of the potentiostat and configuration of the substrate to be coated. Sometimes the area is not known exactly, in which case, potential control is preferred. Also, after initial nucleation of the calcium phosphate crystals within the nanotubes, the deposition can be continued using constant current (−10 mA/cm$^2$) or constant potential (−1.2V). Application of the constant current/potential gives faster deposition rate. Optionally, the electrolyte solution is continuously stirred or deaerated during the deposition. The longer the deposition time the thicker layer as known in the art.

Figure 11:
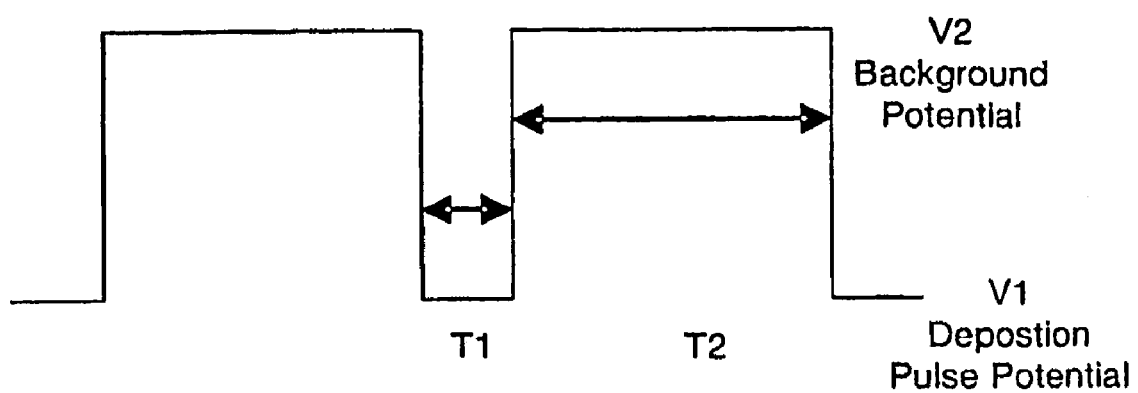
FIG. 11 shows an application of pulsed potential according to an embodiment of the invention.

FIG. 11 shows an application of pulsed potential according to an embodiment of the invention. Referring to FIG. 11, the potential the deposition pulse potential is set to 5.0 V and has a resulting current (I$_1$) in amps and is applied for a pulse time (t$_1$) in seconds. Also, the pulsed potential has a deposition charge (Q$_1$) given by Formula 1 below.

$$Q_1 = I_1 * t_1 \quad \text{Formula 1}$$

A max dwell time (t$_2$) for application of the background potential (V$_2$) can by calculated Formula 2 below:

$$t_2 < 0.5 * (I_1/I_2) * t_1 \quad \text{Formula 2}$$

Where (I$_1$) is the current flowing through the application of (V$_1$) in amps; (I$_2$) is the current flowing through application of (V$_2$) in amps, the charge (Q$_2$) accumulated during application of background potential (V$_2$) is 50% of Q$_1$, as shown in Formula 3 below:

$$Q_2 = 0.5 * Q_1 \quad \text{Formula 3}$$

More preferably, the deposition pulsed potential (V$_1$) may be in the range of about −0.5 to −5.0 V. The background potential may be in the range of about 0 to 0.4 V with reference to open circuit potential. Also, the pulse time (t$_1$) for (V$_1$) may be in the range of about 8 ms to 500 ms and the dwell time (t$_2$) for (V$_2$) may be in the range of about 2 seconds to time required for 50% of Q$_1$ as shown in Formula 3.

Also, with regards to pulsing the deposition pulsed current (I$_1$) may be in the range of about of about −1.0 mA/cm$^2$ to −12 mA/cm$^2$. The range of background current (I$_2$) may be in the range from about 10 μA/cm$^2$ to 1 mA/cm$^2$. The pulse time (t$_1$) for application of the (I$_1$) is the range of about 8 ms to 500 ms. The pulse time (t$_2$) for application of the background current (I$_2$) is in the range of about 2 s to time required for 50% Q$_1$ as shown in Formula 3.

In one aspect of the invention, the potential is pulsed at −1200 mV for about 8 ms to 100 ms and at 0.2 V for about 10 seconds. This cycle may be repeated to obtain the desired thickness. Pulsing the potential allows for improved deposition at the bottom of the nanopores. Pulsing the potentials between −1200 mV and open circuit or anodic potential is a better option for producing nanocrystalline coating. The duration of deposition the potential pulse (−1200 mV) is much shorter than the anodic or open circuit pulse. Similarly, pulsing the current between +10 μA/cm$^2$ (e.g., for 10 sec) to −10 mA/cm$^2$ (e.g., for 100 msec) for varying amounts of time provides uniform growth of nanocrystals of calcium phosphate on anodized valve metal surface. Alternately, a constant current density ranging from about −5 to −12 mA/cm$^2$ can be applied. Continuous stirring and deaeration using pure nitrogen or other inert gas is preferred in order to provide better current or potential control. In either case, the length of the deposition time determines the coating thickness. Typically it takes about an 1 hour at constant potential or current to coat about 10 micron thick coating.

It is noted that any other suitable known technique to form a desired for a desired bioceramic coating on the nanoporous valve metal oxide surface may be used in the invention. For example, other known deposition techniques for hydroxyapatite-based biomaterials may be utilized, such as those described in W. Suchanek and M. Yoshimura, *Processing And Properties Of Hydroxyapatite-Based Biomaterials For Use As Hard Tissue Replacements Implants*, J. Mater. Res., Vol. 13, No. 1, pp. 94-117, January 1998, which is hereby incorporated by reference. Also, the deposition may be electrochemically deposited as described in Oh, et al., *Growth of Nano-Scale Hydroxyapatite using chemically treated titanium oxide nanotubes*, Biomaterials, 26 (2005), pp. 4938-43, which is hereby incorporated by reference. Also, electrochemical deposition as described in Roessler, et al., *Electrochemically Assisted Deposition Of Thin Calcium Phosphate Coatings At Near-Physiological Ph And Temperature"*, (2003), pp. 655-663, Wiley Periodicals, Inc., which is incorporated by reference.

Optionally, the bioceramic coated apparatus is cleaned by conventional methods known in the art. For example, the bioceramic coating may be washed with distilled water.

Figure 3:
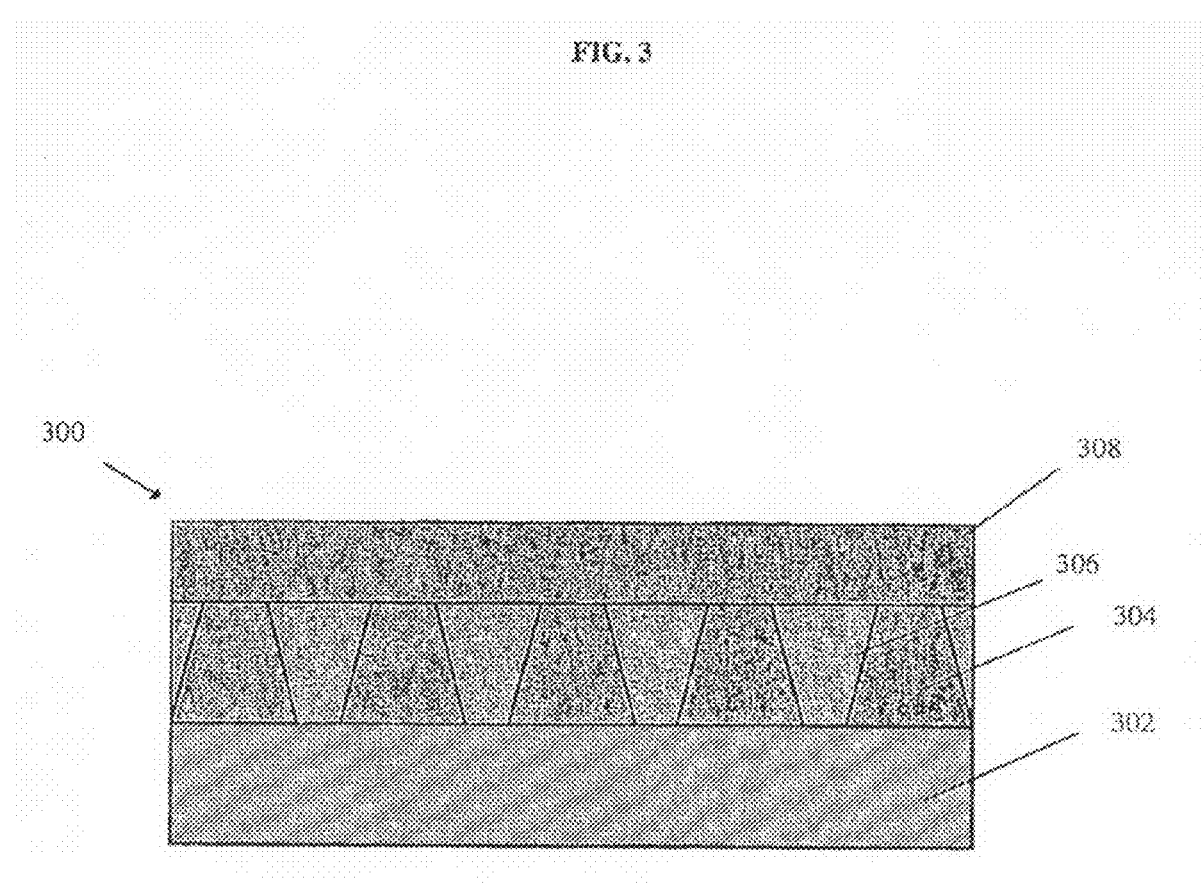
FIG. 3 shows a bioceramic coated apparatus according to an embodiment of the invention.

FIG. 3 illustrates a preferred bioceramic coated apparatus of the invention. Referring to FIG. 3, the bioceramic coated apparatus is generally depicted as reference number 300. The apparatus 300 includes a valve metal substrate 302 having a nanoporous valve metal oxide surface layer 306 containing a plurality of nanopores 304. The nanopores 304 have adsorbed phosphate ions on at least one inner wall of the nanopores. In this embodiment, the nanopores 304 have a substantially tapered shape such that the bottom portion of the nanopores 304 near the valve metal substrate surface 302 are wider than the top portions of the nanopores 304.

A bioceramic coating 308 is formed on the surfaces of nanopores 304 and oxide 306 and is anchored into at least one of the plurality of nanopores 304. Adhesion is improved by forming the bioceramic coating 308 in the nanopores 304 as the tapered shape of the nanopore 304 acts in a mechanical way to aid in the adhesion (e.g., anchor for the coating).

As separate embodiments the invention also relates to a valve metal substrate having a nanoporous substrate and a method of forming a nanoporous surface formed on the valve metal substrate. Each of these, including their preferred embodiments, is described in the context of the bioceramic apparatus and method for forming it. The valve metal substrate is anodized in a fluoride-containing phosphoric acid solution at a voltage and time sufficient to form a nanoporous valve metal oxide surface. The nanopores have adsorbed phosphate ions on at least their interior surfaces.

EXAMPLES

Example 1

Step 1: (Surface preparation): A titanium substrate was mechanically polished using standard metallographic polishing techniques, starting with 120 grit emery paper and incrementally moving to 1200 grit emery paper. More specifically, the titanium substrate was incrementally polished using 120 grit emery paper, 240 grit emery paper, 400 grit emery paper, 600 grit emery paper, and then 1200 grit emery paper. The titanium substrate was about 16 mm in diameter and 1 mm in thickness. After the desired surface was achieved the substrate was wet polished in a 15 micron alumina slurry. Next, the substrate was washed thoroughly with distilled water followed by a sonicate treatment for about 10 minutes in isopropyl alcohol to remove any remaining particles. The polishing was conducted to ensure increased repeatability of experiments described in this example as the starting point of the titanium substrate for each experiment was adjusted to be substantially constant.

Step 2: (Anodization to form the nanoporous surface) The anodization was conducted with a set-up schematically represented in FIG. 1, described above. The titanium substrate from step 1 was immersed in a fluoride-containing phosphoric acid electrolyte solution at room temperature, 0.5 M $H_3PO_4$+5 ml (0.14 M) HF/liter at 24-30° C. The titanium substrate was connected to the positive terminal of the power source and a platinum foil (Pt rod/mesh) having an equal or larger area of the titanium substrate surface was connected to the negative terminal of power source. An external volt meter and an ammeter were connected to the circuit in parallel and series, respectively, for measuring the actual potential and/or current during the anodization process. The distance between the titanium substrate and platinum foil was maintained to about 4 cm.

Figure 4:
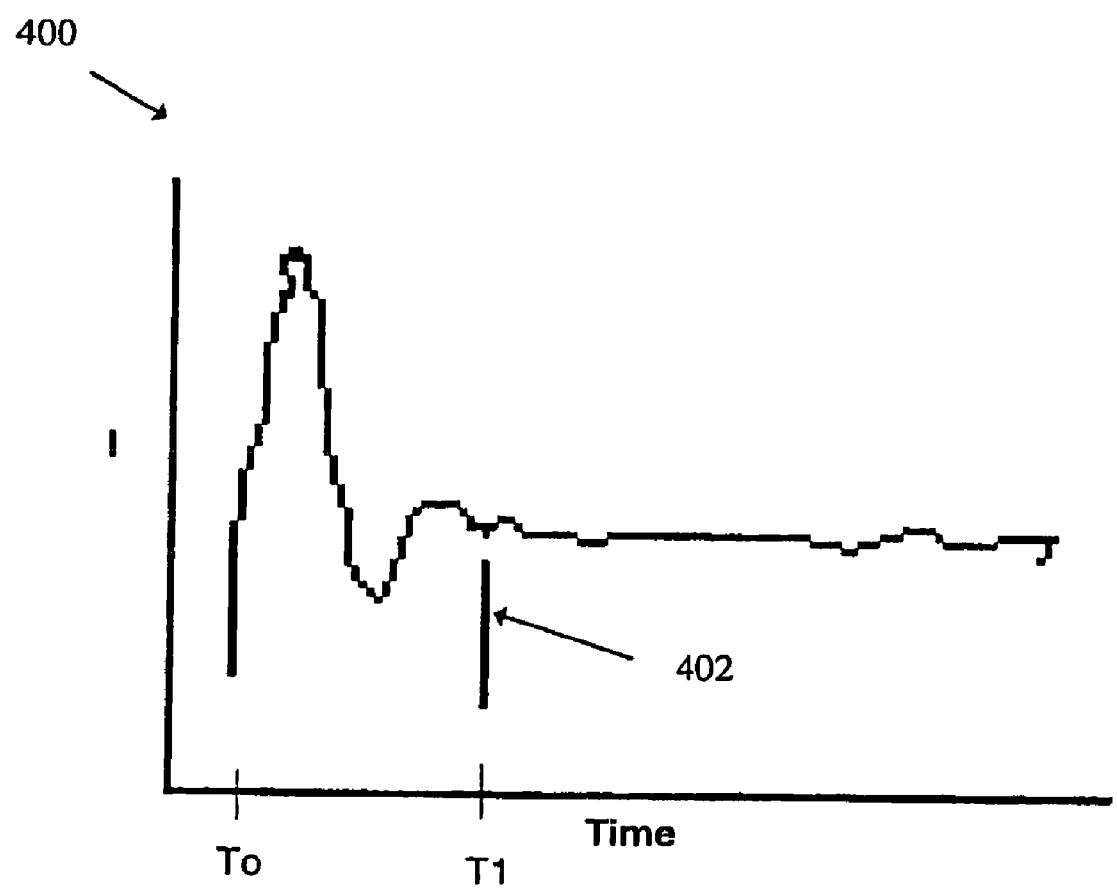
FIG. 4 shows a process for monitoring current versus time during the formation of nanopores according to an example of the invention.

The titanium substrate was initially anodized at a lower voltage of about 10 V to form a nanoporous titanium oxide surface on the titanium substrate. The nanoporous surface had small cylindrical pores with diameters between about 20-50 nm. During the anodization the electrolyte solution was continuously stirred with a magnetic stirrer. During the process the current was monitored as shown in FIG. 4. FIG. 4 shows the process for monitoring current (I) versus time (t) during the formation of nanopores on the titanium substrate. Referring to FIG. 4, initially the current (I) was applied at time ($t_0$) and went through an adjustment period as a portion of the titanium substrate was dissolved, at which point the current plateaued at about 1.22 to about 1.4 $mA/cm^2$ at time ($t_1$) which is about 20 minutes into the process and corresponds to point 402. At point 402, stable nanoporous film growth occurred for about 20 minutes to form a nanoporous to a thickness of about 200 nm.

Figure 5A:
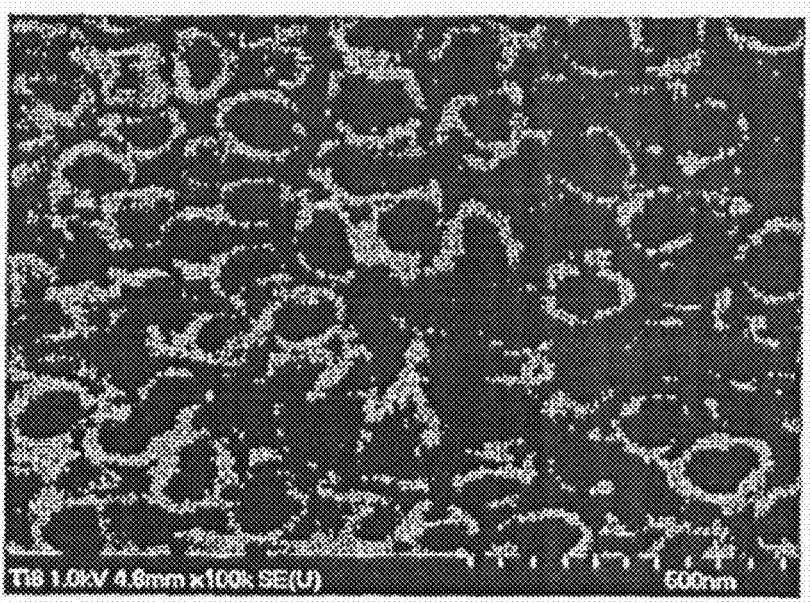
FIGS. 5A and 5B show top down views of SEM photomicrographs at a first and second magnification of nanopores as described in the invention.
Figure 5B:
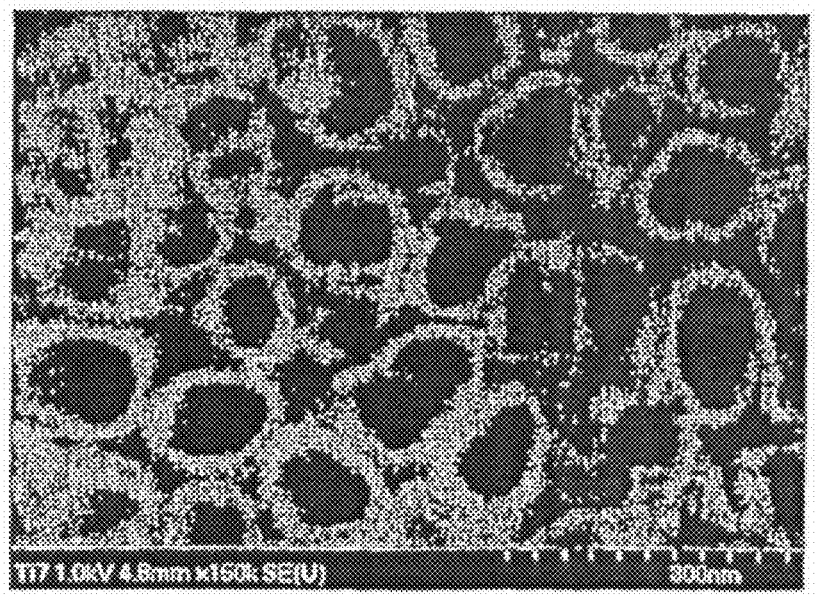
Figure 5C:
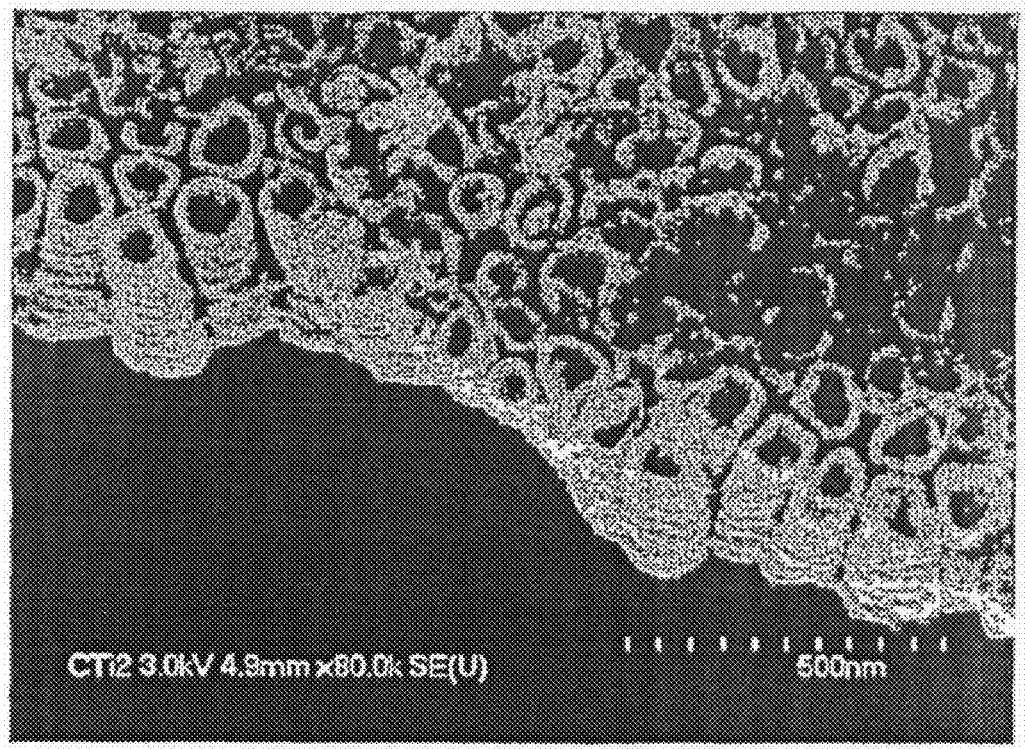
FIGS. 5C and 5D show side views of SEM photomicrographs at a first and second magnification of nanopores as described in the invention.
Figure 5D:
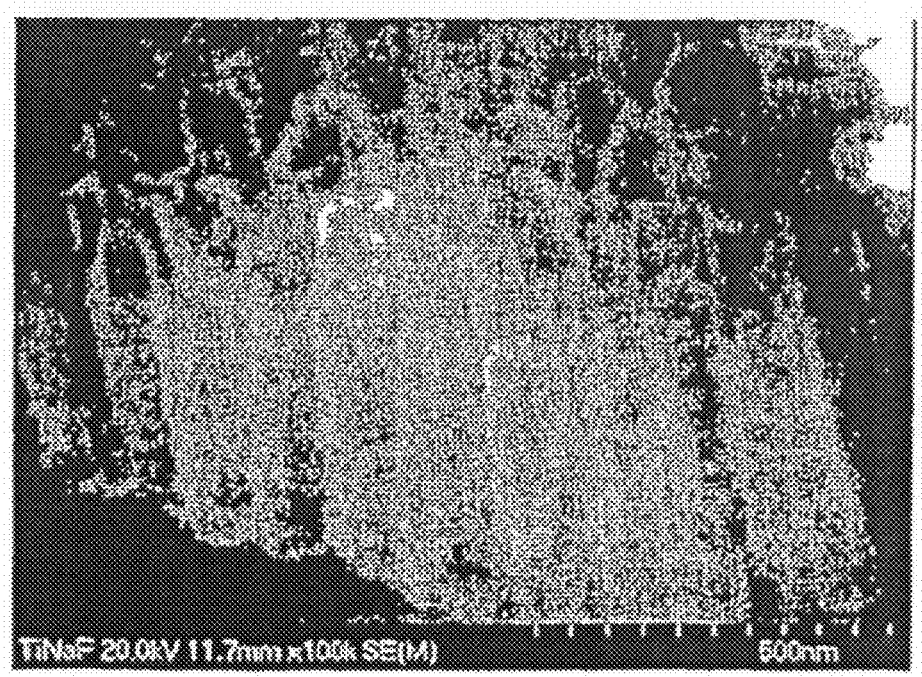

Next, the anodization voltage was increased from 10 V to 20 V at a constant rate of about 0.5 V/min. This controlled increase in voltage resulted in increased diameter nanopores near a bottom portion of the nanopore at the titanium/titanium oxide interface to a diameter of about 60 to 100 nm, thereby forming a substantially tapered shape. Again, during the anodization process the electrolyte was continuously stirred via a magnetic stirring device. FIGS. 5A and 5B are SEM photomicrographs of the nanopores of the nanoporous titanium oxide surface formed during anodization. FIGS. 5A and 5B shows a top down view SEM photomicrographs of nanopores having diameter of about 100 nm at the titanium/titanium oxide interface at a magnification of 100 k and 150 k, respectively. FIGS. 5C and 5D shows side view SEM photomicrographs of the nanopores at a magnification of 80 k and 100 k, respectively.

Step 3: (Washing step): The anodized nanoporous structure was washed in running distilled water for about 10 minutes.

Step 4: (Neutralization step): To prepare the titanium substrate with the nanoporous titanium oxide surface layer for bioceramic coating, the entire substrate was immersed in 0.5 M sodium hydroxide (NaOH) solution for about 15 minutes. This step neutralizes any remaining acid in the nanopores and increases the pH from acidic to neutral or slightly basic (e.g., pH >6.7) inside the pores. Having this pH with in the nanopores aids in the subsequent calcium phosphate bioceramic deposition.

Step 5: (Deposition of bioceramic coating): An electrolyte solution containing calcium and phosphate salts was prepared with the following formulation: 9.5 grams of $Ca(NO_3)_2$+3.0 grams of $NH_4H_2PO_4$+58.5 gram of NaCl+5 grams of calcium phosphate tribasic powder in 1 L distilled water. Also, the pH of the electrolyte solution was adjusted with drops of 1.0 M HCl to arrive at a pH of about 4.

Figure 7A:
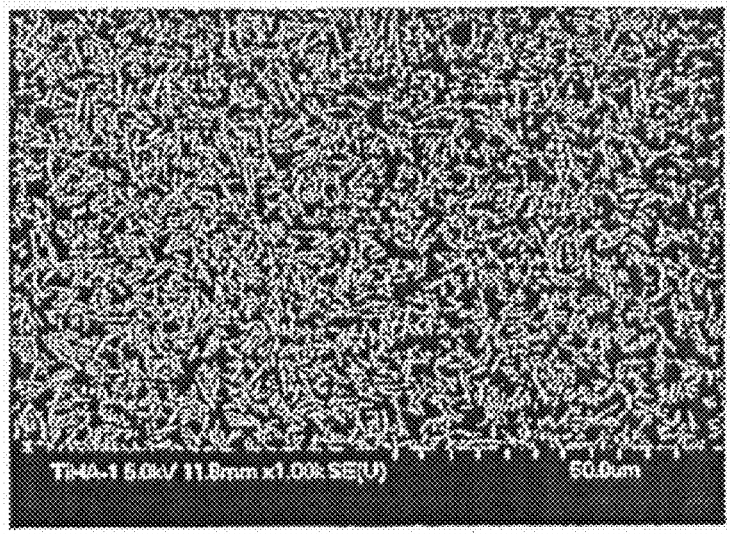
FIGS. 7A-7B shows SEM photomicrographs at a first, second a bioceramic coating as described in Example 1.
Figure 7B:
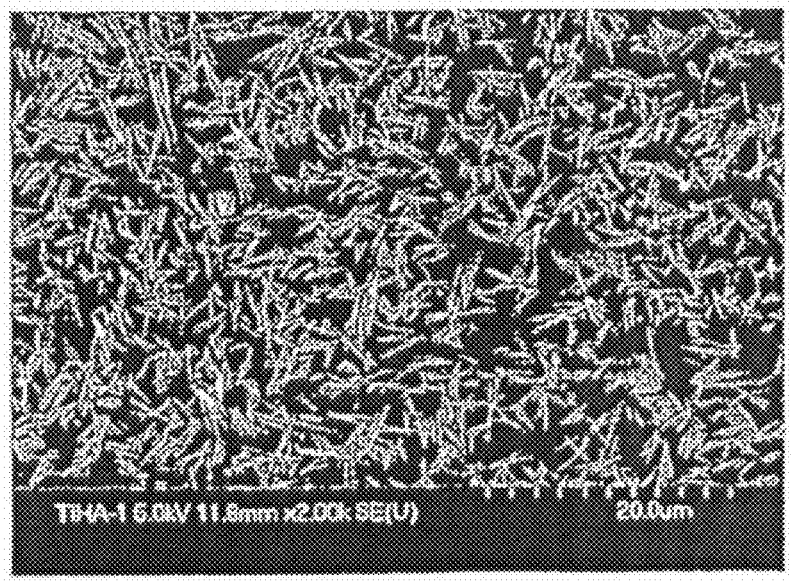

A three electrode set-up, shown in FIG. 2, was used in the electrochemical deposition of the bioceramic coating. A constant potential of about −1200 mV vs Ag/AgCl was applied for 1 hour to form a coating of about 5 μm. During the deposition the electrolyte solution was continuously stirred with a magnetic stirrer. The temperature was maintained at about 80° C. during the deposition. A uniform deposited calcium phosphate bioceramic coating was formed as shown in FIGS. 7A and 7B. The bioceramic coating had a very high adhesive strength due to the use of a substantially tapered nanoporous substrate. The adsorbed phosphate ions on the walls of anodized nanopores resulted in a uniform bioceramic coating due to the nucleation sites they provided.

Example 2

This example initially followed Steps 1 to 4 as described in example 1.

Figure 6:
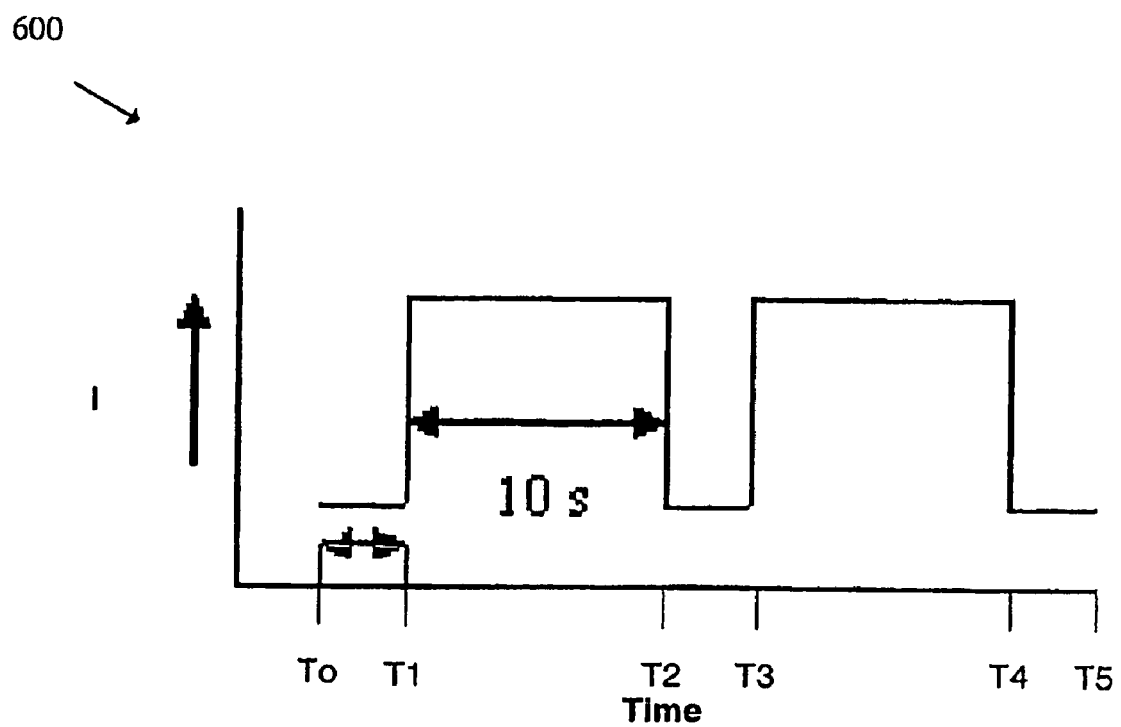
FIG. 6 shows a process for monitoring current versus time during the formation of a bioceramic coating according to an example of the invention.

Step 5: (Deposition of bioceramic coating): A pulsed current deposition was performed utilizing the three electrode set-up, shown in FIG. 2. The temperature of electrolyte solution was maintained at about 80° C. during the pulsed deposition. During the deposition the electrolyte solution was continuously stirred with a magnetic stirrer. During the pulsed deposition process the current was monitored as shown in FIG. 6, which shows current (I) versus time (t) during the calcium phosphate bioceramic coating formation. The current was initially set at $-10$ mA/cm$^2$ at time ($t_0$). After time ($t_1$) had elapsed from time ($t_0$), the current was step increased to 10 μA/cm$^2$, for a time of about 8 ms$\leq(t_1-t_0)$ $\geq$ about 100 ms. After time ($t_2$) had elapsed from time ($t_1$), the current was step decreased to $-10$ mA/cm$^2$ where the difference between ($t_2-t_1$) was about 10 s. The deposition was conducted for about 43 minutes to about form about a 1 μm thick coating. Next, a second deposition at a constant potential was performed as described in step 5 with regards to example 1 above, to form an additional thickness of about 5μm.

Figure 7C:
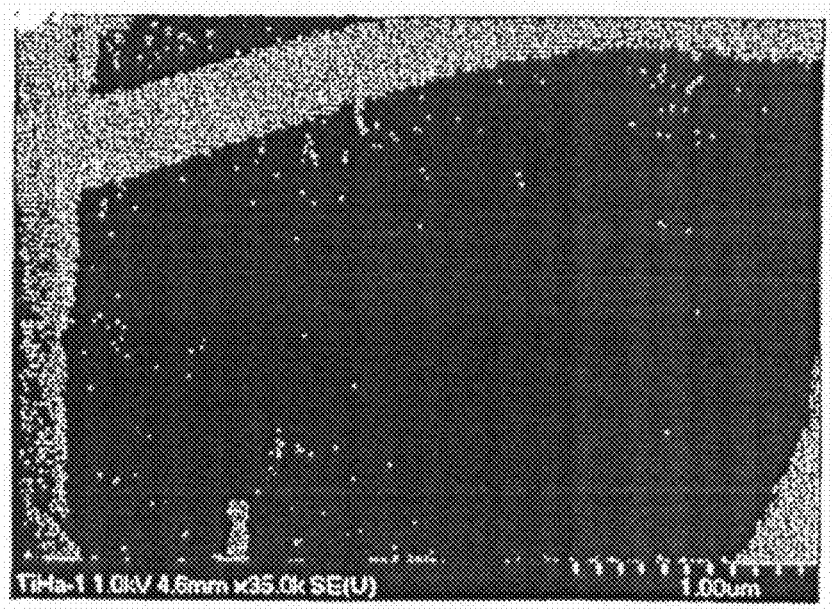
FIG. 7C shows a SEM photomicrograph of a bioceramic coating as described in Example 2.

The bioceramic coating was uniformly deposited as shown in FIG. 7C, an SEM photomicrograph of the bioceramic coating at a magnification of 35K. As can be seen, the bioceramic coating results in nucleation of nanosize calcium phosphate inside nanopores during the pulsing current and large flaky coating is formed during the constant current.

Next, an adhesion test was performed after the electrodeposition the coated surface was washed with distilled water. Using 3M Scotch tape the bond strength was tested qualitatively by sticking the Scotch tape firmly on the coated surface and removing it. This preliminary test indicated good bonding of the bioceramic coating with the titanium oxide nanoporous surface. The coating remained intact on the titanium substrate and only discrete loose calcium phosphate particles stuck to the 3M Scotch tape surface.

The bond strength of the coating was also evaluated by conducting tension testing as described in ASTM standard F 1147-99. The calcium phosphate coated titanium substrate was glued to two mating surfaces using 3M Scotch-Weld 2214-NMF structural adhesive and cured at 121° C. using a suitable fixture at a mild contact pressure. In addition, tensile tests were carried out on a computer-controlled machine at a crosshead speed of 0.25 cm/min (0.1 in/min). The bond strength of the coating was about 16 MPa, which is higher than the standard ISO 13779-2 specified value of 15 MPa. Also, the SEM observation of the tensile tested surface indicated that the coating failed predominantly by cohesive mode. It is noted that part of the coating was still adhered to the substrate after the tensile test.

By way of comparison to the related art it is noted that when electrodeposition of the bioceramic coating was carried out on the polished Ti surface (without nanoporous surface preparation), the bonding between the substrate and coating was very poor, in fact, the deposition was removed during washing and the coating was not uniform.

Figure 8A:
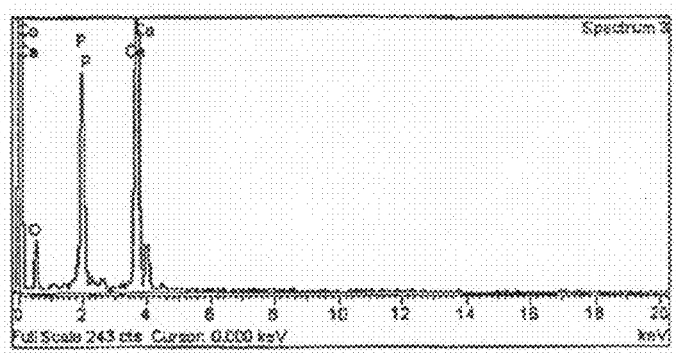
FIG. 8A shows an EDAX analysis of a portion of the bioceramic coating surface as described in Example 3.
Figure 8B:
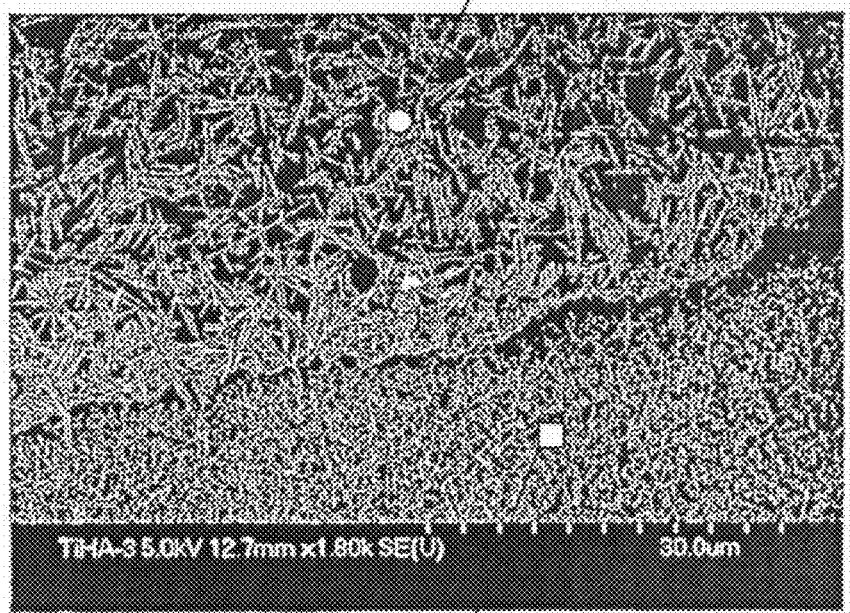
FIG. 8B shows a SEM photomicrograph of the bioceramic coating surface and a portion of the coating removed by scraping as described in Example 3.
Figure 8C:
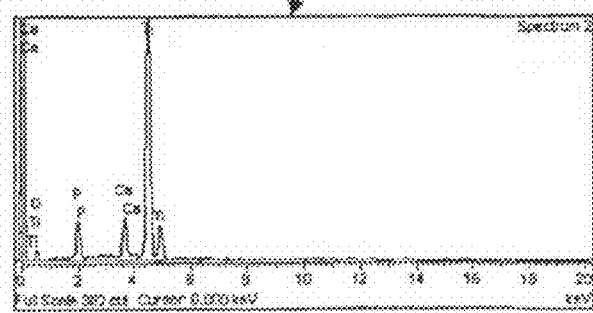
FIG. 8C shows an EDAX analysis of a portion of the bioceramic coating surface of FIG. 9B as described in Example 3.

FIGS. 8A-8C depict the bonding between the nanoporous titanium surface and the bioceramic coating formed in this example. In FIG. 8A, the Energy Dispersive Analytical X-ray (EDAX) analysis shows Ca, P, and O peaks, which were carried out on the bioceramic coating electrodeposited as described above and shown in a portion of FIG. 8B. Also, in FIG. 8B a small portion of the bioceramic coating was scrapped out and an EDAX analysis was carried out on that scraped out portion as well. It is noted that even after scraping, the entire coating did not disbond from the nanoporous surface, also, elemental peaks of Ca, P and O were observed in addition to Ti as shown in the EDAX of FIG. 8C. This observation indicates that bioceramic particles are nucleated from the nanopores imparting better bonding strength. The tapered nanopores of the nanoporous titanium oxide layer and the electrodeposition with pulsed potential (as against a constant potential), results in higher bonding strength.

Example 3

This example initially followed steps 1 to 4 in Example 1.

Step 5: (Deposition of bioceramic coating): An electrolyte solution containing calcium and phosphate salts as follows: (9.5 grams of Ca(NO$_3$)$_2$+3.0 grams of NH$_2$PO$_4$+58.5 gram of NaCl+5 grams of calcium phosphate tribasic powder in IL of distilled water) was prepared. The pH was adjusted with drops of 1.0 M HCL to arrive at a pH of 6.

Figure 7D:
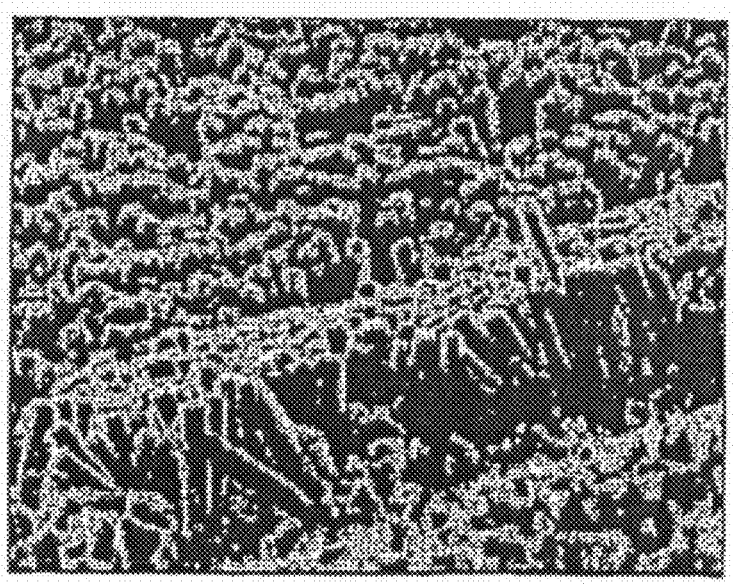
FIG. 7D shows a SEM photomicrograph of a bioceramic coating as described in Example 3.

A three electrode set-up, shown in FIG. 2, and discussed above was used in pulsed mode for the electrochemical deposition in this example. The temperature was maintained at about 80° C. during the pulsed deposition. During the deposition the electrolyte solution was continuously stirred with a magnetic stirrer. During the pulsed deposition process the current was monitored as shown in FIG. 6, as described above. The cycle was repeated for a time period sufficient to form a 3 μm thick coating having toothbrush like bristles. The bioceramic coating obtained is shown in FIG. 7D. As can be see, many of the bristles are vertically oriented, and therefore due to their high surface are extremely useful in aiding biological bone formation. The bioceramic coating also had a very high adhesive strength due to the use of a substantially tapered nanoporous substrate. The adsorbed phosphate ions on the walls of anodized nanopores resulted in a uniform bioceramic coating due to nucleation sites.

An adhesion test was performed after the electrodeposition the bioceramic coated surface was washed with distilled water. Using 3M Scotch tape the bond strength was tested qualitatively by sticking the Scotch tape firmly on the coated surface and removing it. This test indicated good bonding of the bioceramic coating with the Ti surface. The coating remained intact on the titanium substrate and only discrete loose calcium phosphate particles stuck to the Scotch tape surface.

The bond strength of the coating was also evaluated by conducting tension testing as described in ASTM standard F 1147-99. The calcium phosphate coated Ti substrate was glued to two mating surfaces using 3M Scotch-Weld 2214-NMF structural adhesive and cured at 121° C. using a suitable fixture at a mild contact pressure. In addition, tensile tests were carried out on a computer-controlled machine at a crosshead speed of 0.25 cm/min (0.1 in/min). The bond strength of the coating was about 19 MPa, which is higher than the standard ISO 13779-2 specified value of 15 MPa. Also, the SEM observation of the tensile tested surface indicated that the coating failed predominantly by cohesive mode. It is noted that part of the coating was still adhered to the substrate after the tensile test.

Example 4

Figure 9:
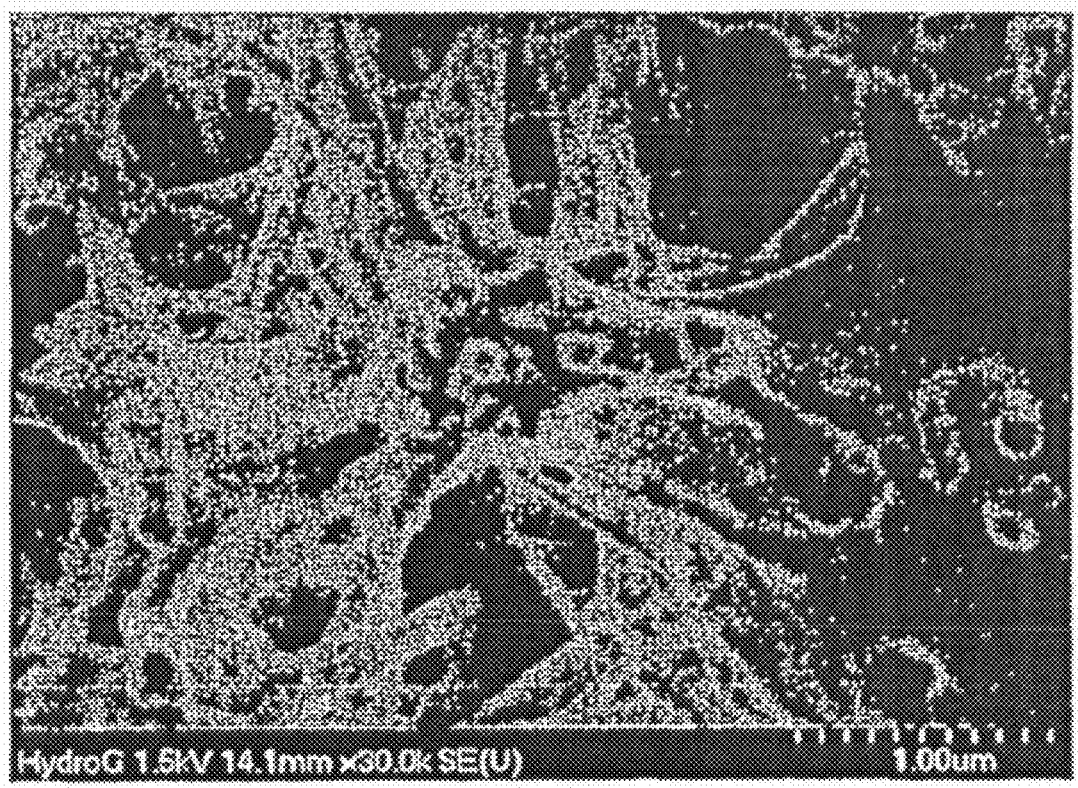
FIG. 9 shows a SEM photomicrograph of the bioceramic coating surface as described in Example 4.

This examples shows cell growth on the calcium phosphate bioceramic coated nanoporous substrates of the invention. The cell culture study was conducted on a calcium phosphate bioceramic coated substrate of Example 1 using the American Type Culture Collection, human embryonic palatal mesenchyme cells (HEPM), catalogue # CRL-1486. The culture medium was Dulbecco's modified Eagle's medium (DMEM) and consisted of 7% Fetal Bovine Serum (FBS), 1% antibiotic-antimycotic, 50 μg/ml ascorbic acid and 0.11 g/l sodium pyruvate. The subculturing medium was DMEM and consisted of 2% Fetal Bovine Serum (FBS), 1% antibiotic-antimycotic, 50 µg/ml ascorbic acid and 4 mM β-gycerophosphate. A 2 ml of the cell suspension was plated per well of a 12-well plate containing calcium phosphate coated samples with a seeding density of 97500 cells per ml. Appropriate quantity of the cell suspension was plated per well of a 12-well plate containing calcium phosphate coated samples. The wells were seeded with 97500 cells per ml. The cells were incubated at 37° C. in an atmosphere of 95% air and 5% $CO_2$. The time taken for the monolayer formation was recorded. Each day the growth of the cells was monitored. After 2 days of cell growth, the samples were observed under a scanning electron microscope. The results are shown in FIG. 9, and show the morphology of CRL-1486 cells grown on calcium phosphate coating for 2 days. The bone cells have adhered well and spread out uniformly on the calcium phosphate coating.

Example 5

This example illustrates the development of a thinner amorphous calcium phosphate (ACP) coating process at relatively low temperatures of about 24-37° C. Also, this process can be used as a surface preparation step for thicker electrodeposition of calcium phosphate coating such as described in Example 2. This example initially follows steps 1 to 3 in Example 1.

Step 4: (Bioceramic deposition): The nanoporous titanium substrate was immersed in an electrolyte solution containing [phosphoric acid (0.3 M) or sodium phosphate (0.3 M)]+fluoride (0.14 M)+calcium nitrate (0.1 M). When phosphoric acid was used the pH was 2.0, when sodium phosphate was used the pH was 2.0, but was adjusted by adding 1.0 M nitric acid to a pH of about 3.0. A two electrode configuration, as described in FIG. 2, was used. The temperature was maintained at about 24° C. during the deposition. Also, during the deposition the electrolyte solution was continuously stirred with a magnetic stirrer. A constant potential of about 20 V for 30 minutes was applied on the nanoporous titanium surface for about 30 minutes to form a coating having a thickness of about 100 nm.

Figure 10A:
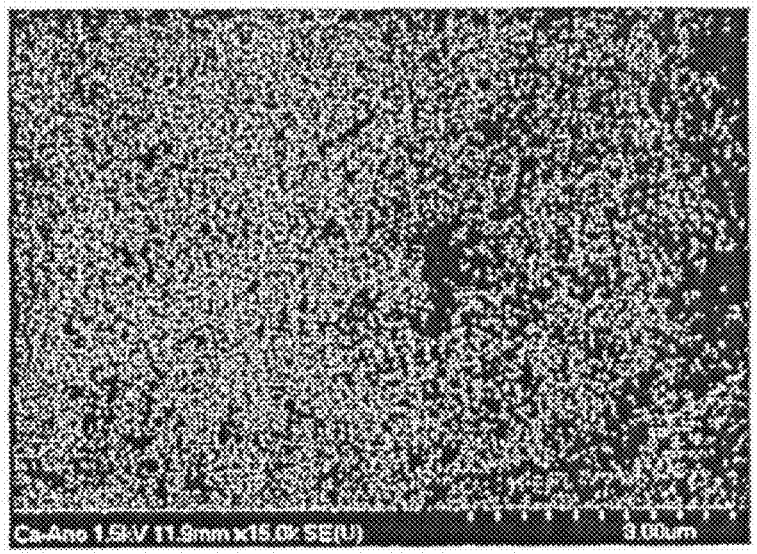
FIGS. 10A and 10B shows SEM photomicrograph at a first and second magnification of a bioceramic coating as described in Example 5.
Figure 10B:
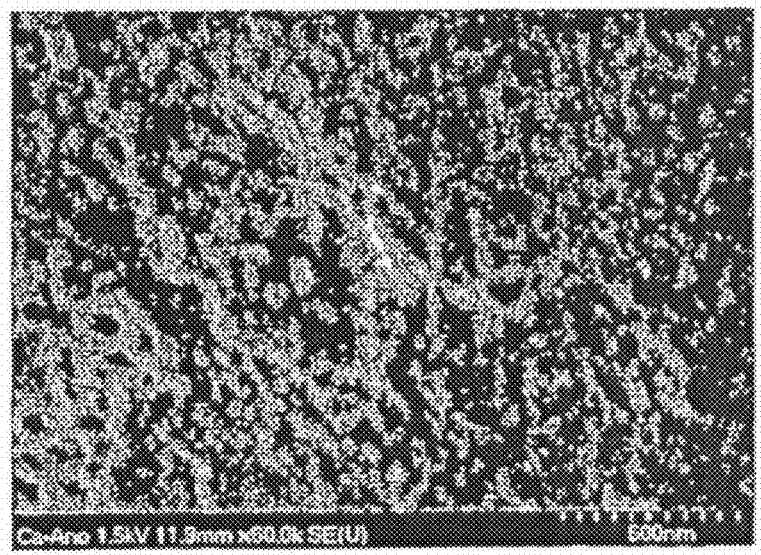

FIG. 10A is an SEM photomicrograph showing the morphology of the calcium phosphate coating deposited at room temperature on the anodic nanoporous titanium oxide surface at 15 k magnification. FIG. 10B show the morphology of calcium coating at 60 k magnification. The calcium phosphate coating obtained was amorphous in structure because of the low temperature deposition procedure. Adhesive tape bond strength testing method showed very high bond strength of this coating.

What is claimed:

1. A bioceramic coated apparatus, comprising:
 a valve metal substrate having a nanoporous valve metal oxide surface layer containing a plurality of nanopores, wherein the nanopores have adsorbed phosphate ions on at least their interior surfaces; and
 a bioceramic coating formed on the nanoporous surface and anchored into the nanopores.

2. The bioceramic coated apparatus of claim 1, wherein the plurality of nanopores have a substantially tapered shape such that a bottom portion of the nanopores is wider than a top portion of the nanopores.

3. The bioceramic coated apparatus of claim 1, wherein the bioceramic coated apparatus is a medical implant.

4. The bioceramic coated apparatus of claim 1, wherein the valve metal is titanium or a titanium alloy.

5. The bioceramic coated apparatus of claim 1, wherein the bioceramic coating is formed to thickness ranging from about 10 nm to about 25 µm.

6. The bioceramic coated apparatus of claim 1, wherein the bioceramic coating has a Ca/P ratio from about 1.5 to about 1.7.

7. The bioceramic coated apparatus of claim 1, wherein the bioceramic coating is a hydroxyapatite coating.

8. A method for forming a bioceramic coated apparatus, comprising the steps of:
 anodizing a valve metal substrate in a fluoride-containing phosphoric acid solution at a voltage and time sufficient to form a nanoporous valve metal oxide surface on the valve metal substrate, wherein the nanopores have adsorbed phosphate ions on at least their interior surfaces;
 contacting the nanoporous valve metal oxide surface with a basic solution to raise the pH to or above about 6.7;
 immersing the nanoporous valve metal oxide surface in an electrolyte solution containing calcium and phosphate ions; and
 electrodepositing a calcium phosphate ceramic surface on the nanoporous valve metal oxide surface.

9. The method of claim 8, further comprising the step of increasing the voltage at a rate sufficient to form the nanopores in a substantially tapered shape.

10. The method of claim 8 or 9, wherein the fluoride-containing phosphoric acid solution has a phosphoric acid concentration ranging from about 0.1 M to about 5.0 M and a fluoride ion concentration ranging from about 0.1 M to about 0.3 M; and wherein the anodization step at a solution temperature ranging from about 24 to about 30° C.

11. The method of claim 10, wherein the valve metal is titanium or a titanium alloy.

12. The method of claim 8 or 9, wherein the electrolyte solution contains salts selected from the group consisting of $Ca(NO_3)_2$, calcium acetate, $NH_4H_2PO_4$, calcium glycerphosphate, calcium phosphate tribasic powder, and combinations thereof.

13. The method of claim 8 or 9, wherein the electrodepositing step comprises applying a pulsed current or potential to deposit the calcium phosphate ceramic surface and, optionally, wherein the electrolyte solution is continuously stirred or deaerated during the deposition.

14. The method of claim 8 or 9, wherein the electrolyte solution has a pH ranging from about 4.0 to about 6.0.

15. The method of claim 8 or 9, wherein the bioceramic coating is formed to a thickness ranging from about 10 nm to 25 µm.

16. The method of claim 15, wherein the bioceramic coating has a Ca/P ratio from about 1.5 to about 1.7.

17. A bioceramic coated apparatus formed by the process of claim 16.

18. The bioceramic coated apparatus of claim 17, wherein the apparatus is a medical implant.

19. A method for forming a nanoporous surface on a surface of a valve metal, comprising the step of:
 anodizing a valve metal surface in a fluoride-containing phosphoric acid solution at a voltage and time sufficient to form a nanoporous valve metal oxide surface on the valve metal substrate, wherein the nanopores have adsorbed phosphate ions on at least their interior surfaces.

20. The method of claim 19, further comprising the step of increasing the voltage at a rate sufficient to form the nanopores in a substantially tapered shape.

21. The method of claim 19 or 20, wherein the fluoride-containing phosphoric acid solution has a phosphoric acid concentration ranging from about 0.1 M to about 5.0 M and a fluoride ion concentration ranging from about 0.1 M to about 0.3 M; and wherein the anodization step is done in the fluoride-containing phosphoric acid solution having a temperature ranging from about 24 to about 30 ° C.

22. The method of claim 21, wherein the valve metal is titanium or a titanium alloy.

23. The method of claim 20, herein the voltage is increased at a substantially constant rate at about 0.5 V/min from about 10 V to 20 V.

24. The method of claim 19 or 20, wherein the nanopores are substantially uniform in shape.

25. A valve metal substrate comprising a nanoporous valve metal oxide surface layer containing a plurality of nanopores, wherein the nanopores have adsorbed phosphate ions on at least their interior surfaces.

26. A valve metal substrate of claim 25, further comprising a calcium phosphate ceramic surface on the nanoporous valve metal oxide surface.

27. The valve metal substrate of claim 25, wherein the plurality of nanopores have a substantially tapered shape such that a bottom portion of the nanopores is wider than a top portion of the nanopores.

28. The valve metal substrate of claim 25, wherein the valve metal is titanium or a titanium alloy.

29. A valve metal substrate comprising a nanoporous valve metal oxide surface layer containing a plurality of nanopores, wherein the nanopores have adsorbed phosphate ions on at least their interior surfaces and the nanopores have a substantially tapered shape such that a bottom portion of the nanopores is wider than a top portion of the nanopores.

30. The valve metal substrate of claim 29, wherein the valve metal is titanium or a titanium alloy.

* * * * *

UNITED STATES PATENT AND TRADEMARK OFFICE
CERTIFICATE OF CORRECTION

| | | |
|---|---|---|
| PATENT NO. | : 7,998,568 B2 | |
| APPLICATION NO. | : 11/570935 | |
| DATED | : August 16, 2011 | |
| INVENTOR(S) | : Krishnan Selva Raja, Manoranjan Misra and Archana Kar | |

It is certified that error appears in the above-identified patent and that said Letters Patent is hereby corrected as shown below:

In the Specification

On Column 1, Line 12, before the "Background of the Invention," please insert the following paragraph:
--ACKNOWLEDGMENT OF GOVERNMENT SUPPORT
This invention was made with government support under Grant No. DE-FC52-98NV13492 and DE-FG02-04ER63819 awarded by the Department of Energy. The government has certain rights in the invention.--

Signed and Sealed this
Twenty-sixth Day of November, 2024

Katherine Kelly Vidal
*Director of the United States Patent and Trademark Office*